United States Patent [19]

Flatland

[11] 4,121,342
[45] Oct. 24, 1978

[54] TELESCOPING HANDPIECE

[76] Inventor: Lloyd P. Flatland, 15 Quisisana Dr., Kentfield, Calif. 94904

[21] Appl. No.: 722,482

[22] Filed: Sep. 13, 1976

[51] Int. Cl.² ............................................. A61C 1/10
[52] U.S. Cl. ..................................................... 32/26
[58] Field of Search .................. 32/26, 27; 74/750 R, 74/798; 192/108, 67 R

[56] References Cited

U.S. PATENT DOCUMENTS

| | | | |
|---|---|---|---|
| 184,992 | 12/1876 | Starr | 192/67 R |
| 219,849 | 9/1879 | Cushing | 32/26 |
| 1,355,659 | 10/1920 | Evslin | 192/67 R |
| 1,376,952 | 5/1921 | Lindholm | 192/67 R |
| 2,536,803 | 1/1951 | Gleason | 74/798 |
| 3,400,459 | 9/1968 | Stemler | 32/26 |
| 3,942,392 | 3/1976 | Page, Jr. et al. | 74/750 R |

FOREIGN PATENT DOCUMENTS 1,054,661  3/1959  Fed. Rep. of Germany .............. 32/26
276,939  8/1927  United Kingdom ........................ 32/26

Primary Examiner—Louis G. Mancene
Assistant Examiner—John J. Wilson
Attorney, Agent, or Firm—Lothrop & West

[57] ABSTRACT

A handpiece for dental use has primary and secondary housings arranged concentrically and slidably with respect to each other. A primary drive shaft mounted to rotate within the primary housing is connected slidably, preferably by splines, with a secondary drive shaft mounted to rotate within the secondary housing so that the handpiece can be extended and retracted for work. The primary housing may also have a planetary transmission, the planets in which drive a quill concentric with a motor shaft mounted to rotate in the primary housing and connected to the transmission. The primary shaft is slidable to engage the motor shaft directly and alternatively to engage the quill. Controls accessible from the exterior of the housings are effective to slide the housings relative to each other and to engage and disengage the planetary transmission and the motor shaft.

3 Claims, 11 Drawing Figures

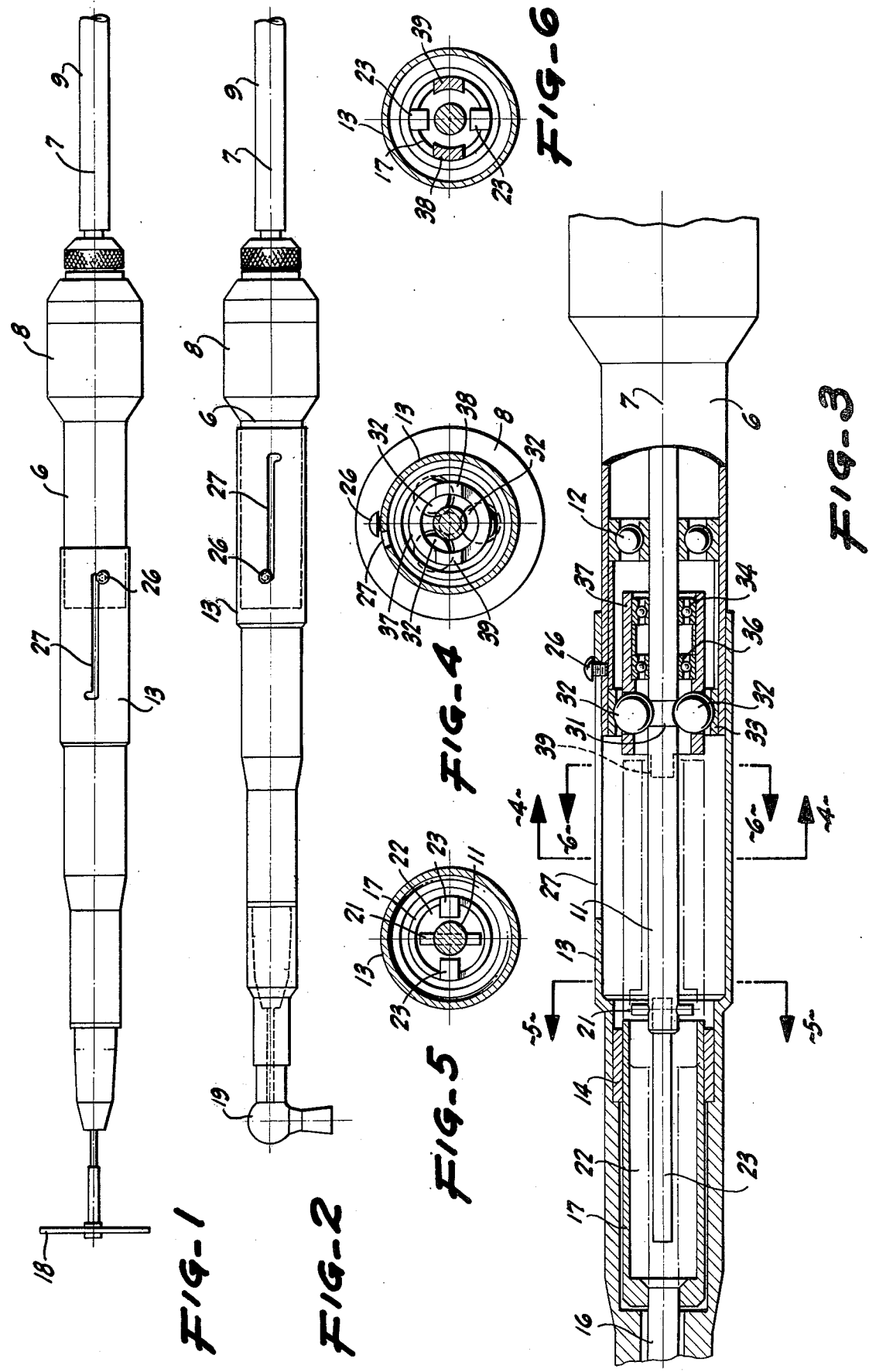

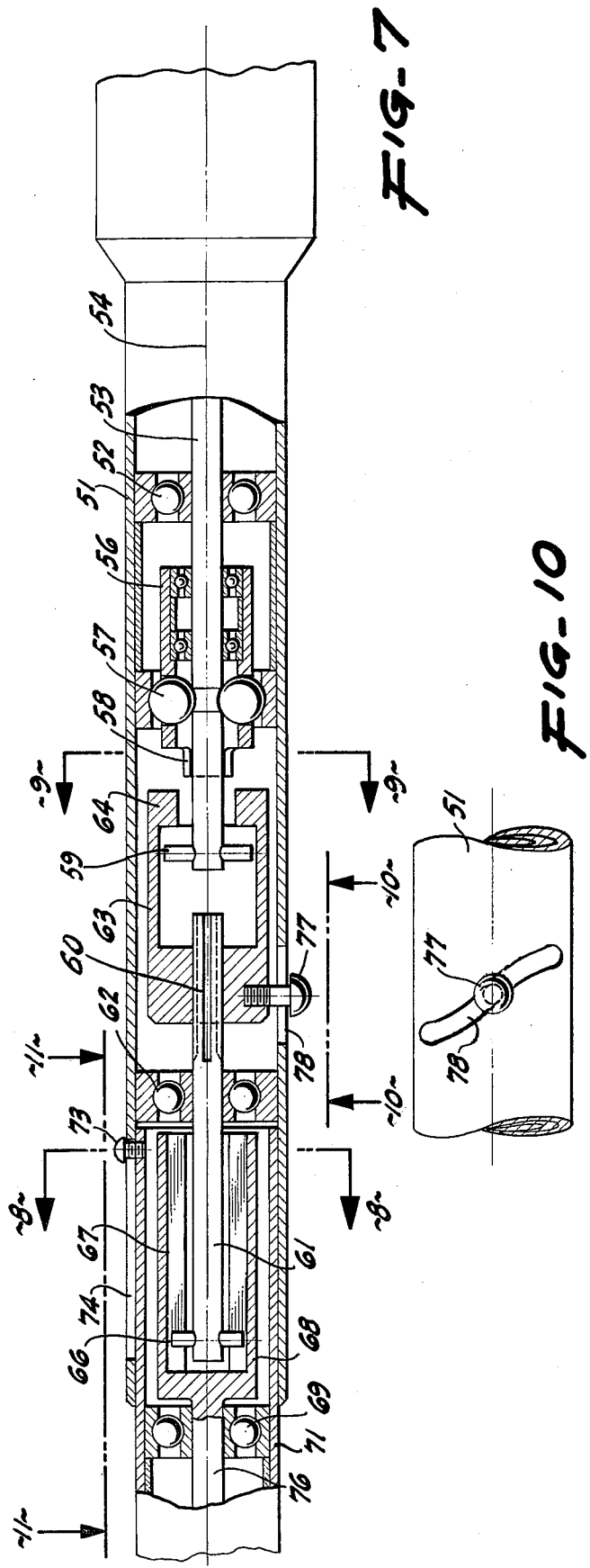
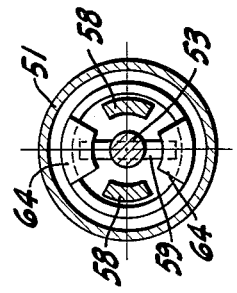
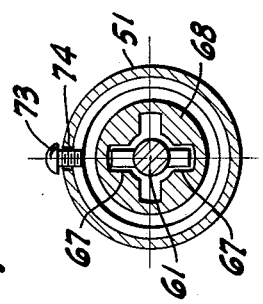
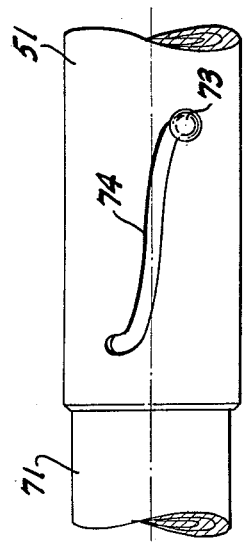

TELESCOPING HANDPIECE

BRIEF SUMMARY OF THE INVENTION

For use as a handpiece in dentistry there is provided a pair of telescoping housings, each containing a rotatable shaft appropriately driven by a motor shaft and the shafts themselves being connected for continuous rotation but being slidably engaged. An exterior control regulates the sliding movement. One of the housings may contain a planetary or comparable transmission affording two speeds of rotation. An exterior control regulates the effective speed of rotation by regulating the transmission.

BRIEF DESCRIPTION OF THE SEVERAL VIEWS OF THE DRAWINGS

FIG. 1 is a side elevation of a dental handpiece constructed pursuant to the invention and in its extended position.

FIG. 2 is a view comparable to FIG. 1 but showing the handpiece in its retracted position.

FIG. 3 is an enlarged view comparable to FIG. 1 but with portions broken away to show the interior construction on an axial or longitudinal plane.

FIG. 4 is a detail showing the parts in cross-section, the plane of which is indicated by the line 4—4 of FIG. 3.

FIG. 5 is a detail cross-section, the plane of which is indicated by the line 5—5 of FIG. 3.

FIG. 6 is a cross-section, the plane of which is indicated by the line 6—6 of FIG. 3 and showing the interior parts in a retracted position of the housings.

FIG. 7 is a view comparable to FIG. 3 but showing a modified form of device.

FIG. 8 is a cross-section, the plane of which is indicated by the line 8—8 of FIG. 7.

FIG. 9 is a cross-section, the plane of which is indicated by the line 9—9 of FIG. 7.

FIG. 10 is a detail view showing one of the externally available controls.

FIG. 11 is a detail view showing another of the exteriorly available controls.

DETAILED DESCRIPTION

In the utilization of a dental handpiece, it is customary to apply tools of different sorts to the end of the handpiece for various dental operations. These tools vary a good deal in their weight and in their axial extent. A difficulty arises in that the handpiece should normally be quite well balanced to reduce fatigue on the part of the dental operator and to afford appropriate access to the mouth cavity of the patient. It occurs in many instances that when different attachments are applied to the handpiece the balance is substantially interfered with and results in comparable fatigue to the operator. Furthermore, sometimes the location of the attachment on the handpiece makes it difficult to operate within the patient's mouth.

It is therefore an object of the invention to provide a dental handpiece which can be projected and retracted or slidably or telescopically operated so that when a relatively heavy or long attachment is applied the handpiece can be made short and, conversely, when a relatively light or short attachment is utilized the handpiece itself can be extended. In any case the handpiece length can be projected or retracted in order best to acommodate the tool for the dentist's use in the patient's mouth.

Another object of the invention is to provide in a dental handpiece an arrangement in which the driving shaft or motor shaft can be connected to the driven or secondary shaft in either one of at least two ways so that the speed and torque at the dental tool can be varied with respect to the speed and torque available from the driving motor. Both the extension and retraction and the particular drive and tool relationship are preferably readily controllable by the dentist from the exterior without any particular tools and without halting his work.

In one form of the invention, as especially illustrated in FIGS. 1–6 herein, there is afforded a handpiece inclusive of a primary housing 6 symmetrical with a longitudinal axis 7 and usually made with a circular cross-section. The housing 6 is directly connected to the casing 8 of a drive motor or the like (not shown) concentric with the axis 7 and customarily constituted by an engine or turbine operated by air from an air source 9. Within the primary housing 6 there is a primary shaft 11 supported for rotation about the axis 7 in a suitable bearing 12 fixed in the primary housing 6.

Surrounding the primary housing 6 and slidable with respect thereto with an easy frictional fit is a secondary housing 13, also concentric with the axis 7 and carrying a bushing 14 in which a secondary shaft 16 is rotatable mounted. The shaft 16 includes a secondary tube 17, preferably integral with or fixed on the shaft 16 and extending along the axis 7. The shaft 16 terminates in an appropriate collet or chuck or the like, not shown, designed to receive any one of several different kinds of dental tools such as 18 and 19 in FIGS. 1 and 2. These tools are removable and replaceable in the customary fashion but when connected are each turned by the secondary shaft 16. In order properly to interrelate the parts, the primary shaft 11 at one end is provided with splines 21, preferably in the form of an oppositely extending diametral pin. The splines are receivable in spaces 22 within the member 17 and are then disposed between a pair of longitudinally extending, inwardly directed splines 23, preferably forming part of the tube 17.

The primary housing 6 and the secondary housing 13 are kept from relative rotation but are afforded axial telescoping movement by a control 26 fast in the housing 6 and arranged to slide in a scroll opening 27 in the housing 13, the configuration being such as to afford a longitudinal central slot and offset portions at the ends thereof.

With this mechanism the dentist at any time can telescope the housing 6 with respect to the housing 13, such movement being accompanied by sliding movement of the external splines 21 between the internal splines 23. There is substantial lost motion circumferentially between the splines 21 and 23, but nevertheless the splines interengage to transmit rotation in any longitudinally or axially displaced position of the housing 13 on or with respect to the housing 6. In this way the operator can move the housings into any selected positions.

While there is an infinite number of such positions, it is usually sufficient to utilize just the two end positions and hence the offset portions of the scroll opening 27 permit, upon slight relative rotation of the housings, the parts to be interengaged in either end position against inadvertent axial sliding. Thus, when a relatively light tool 18 is to be employed the housings are spread or lengthened with respect to each other to preserve the desired balance. When a relatively heavy tool 19 is applied to the end, the handpiece is withdrawn or collapsed so that it is relatively short and the balance is still maintained.

Under some circumstances it is desired not only to have the handpiece telescope but likewise to afford different drive speed and torque transmission in one position as distinguished from the other. Under those circumstances the primary shaft 11 is provided with a reduced portion 31 (FIG. 3) which in effect serves as a sun member in a frictional planetary transmission. In engagement with the sun portion are planetary balls 32 also in frictional engagement with a planetary ring 33 fixed within the primary housing 6. Supported on the shaft 11 by bearings 34 and 36 is a quill 37 concentric with and rotatable about the axis 7 and in engagement with the planetary balls 32 by virtue of conforming openings in the quill in close engagement with the exterior of the balls. The quill is extended to provide a pair of diametrically opposite clutch teeth 38 and 39 (FIG. 6) extending axially from the end of the quill.

Adapted to cooperate with the clutch teeth are the internal splines 23 of the tube 17. When the parts are in the extended position shown in FIG. 3, the internal splines 23 are spaced from the teeth 38 and 39 and are declutched therefrom. Torque transmission is then directly from the primary shaft 11 through the splines 21 and to the splines 23, as previously described. When, however, the housings 6 and 13 are contracted with respect to each other, the internal splines 23 are moved into the position shown in dotted lines in FIG. 3 with the splines 23 in the path of rotation of the extended clutch teeth 39 and 38. The splines 21 are disconnected and the quill is directly connected to the splines 23 in the tube 17. In this position of the tube 17, the splines 23 have advanced past the external splines 21 so that there is no longer any drive transmitted from the splines 21 to the internal splines 23, but the clutch teeth 38 do transmit torque directly from the quill 37 to the tube 17. Because of the reduction in speed and increase in torque due to the frictional planetary transmission, the tool is better adapted to some classes of work.

The operator, in order to take advantage of the high torque, need only shorten the handpiece to cause interengagement of the planetary transmission and the driven tube 17 on the secondary shaft 16.

The structure can be arranged so that the torque transmitted is independent of the length of the handpiece.

As particularly shown in FIGS. 7-11 inclusive, the primary housing 51 has a bearing 52 supporting a shaft 53 connected to the motor in the casing 8 and rotatable about the longitudinal axis 54 of the structure. Around the motor shaft is mounted a quill 56 driven from the motor shaft through a frictional planetary transmission, including balls 57, as previously described. One end of the quill has clutch teeth 58 thereon. The end of the motor shaft 53 also has external splines 59 thereon. A primary shaft 61 is mounted in the housing 51 by means of a bearing 62 and through interengaging splines 60 carries a driven tube 63, also having interior splines 64 or clutch teeth. When the tube 63 is moved axially on the axially fixed shaft 61 and with respect to the housing 51 the internal splines 64 can be engaged with the external splines 59 and the motor shaft 53, or, after going through an intermediate neutral position, can be interengaged with the clutch teeth 58 on the quill 56.

The primary shaft 61 at its outer end is provided with external splines 66 in the form of a through rod interengaging with the longitudinal internal splines 67 in a driven tube 68. This is carried by a bearing 69 in a secondary housing 71 slidable within the housing 51 under the control of a pin 73 operating in a slot 74. The driven member 68 is integral with or continued by a secondary shaft 76 arranged to be connected to appropriate dental tools, as before.

In this structure the tube 63 is axially positioned by means of an externally available control 77 operating in a short scroll slot 78 in the housing 51. The control 77 moves between one extreme position in which the internal splines 64 engage the clutch teeth 58 and another extreme position in which the internal splines 64 engage the external splines 59. The external splines 66 always stay in engagement with the internal splines 67 within the secondary housing 71.

With this arrangement the secondary housing can be moved axially with respect to the primary housing simply by moving the control 73 to and fro in the slot 74, the interengaged splines 66 and 67 allowing for this lengthening and shortening movement without disturbing the rest of the mechanism. The balance of the handpiece can thus be adjusted by setting any desired axially spaced, relative position of the primary and secondary housings. Also, by properly manipulating the externally available control 77, the driven tube 63 can be moved from a neutral position in one direction to engage directly with the splines 59 so that there is a straight through drive from the motor shaft 53. If an increased torque and reduced speed is necessary or desirable, the control 77 can be moved into an opposite position so that the external splines 59 are disengaged. The drive is then through the frictional planetary transmission and through the quill 56 to the driven tube 63 and so to the primary shaft 61 and then to the secondary shaft 76. With this form of device any combination of handpiece length and available driving torque can be selected by the operator.

I claim:

1. A telescoping handpiece adapted interchangeably to engage tools of different lengths and weights comprising a primary housing, a primary shaft, means for mounting said primary shaft in said primary housing for rotation and against translation relative to said primary housing, means associated with said primary housing for rotating said primary shaft, a secondary housing slidably mounted with respect to said primary housing, a secondary shaft including a secondary tube, means for mounting said secondary shaft in said secondary housing for rotation and against translation relative to said secondary housing, inwardly directed longitudinally extending splines in said secondary tube, external splines on said primary shaft engageable with said inwardly directed splines, means for selectively interconnecting said external splines with different axial portions of said internal splines upon relative axial sliding movement of said primary housing and said secondary housing, said internal splines stopping short of the end of said secondary tube to leave an axial gap and said external splines on said primary shaft being movable out of and into said gap for rotatably clutching and declutching said primary shaft and said secondary shaft, a planetary transmission between said primary shaft and said primary housing, said transmission including planet members, a quill surrounding said primary shaft and engaging said planet members for rotation therewith, axial teeth on said quill, axially extended splines on said secondary tube, and means for axially moving said secondary tube for engaging said axially extended splines with said axial teeth and moving said external splines into said gap and alternatively for disengaging said axially extended splines from said axial teeth and engaging said internal and external splines for clutching and declutching said quill and said primary shaft.

2. A device as in claim 1 including means for axially sliding said secondary shaft a substantial distance in engagement with said primary shaft with said primary shaft disengaged from said quill.

3. A device as in claim 1 in which said secondary housing and said secondary shaft are axially slidable relative to said primary housing and said primary shaft through distances effective to change substantially the overall length and balance of said handpiece in amounts compensating for changes in balance caused by the use of said tools of different lengths and weights.

* * * * *